United States Patent
Resconi

(10) Patent No.: US 6,441,211 B1
(45) Date of Patent: Aug. 27, 2002

(54) PREPARATION OF TRANSITION-METAL-ALKYL-COMPLEXES CARRYING A BIDENTATE, DIANIONIC LIGAND

(75) Inventor: Luigi Resconi, Ferrara (IT)

(73) Assignee: Basell Technology Company BV (NL)

( * ) Notice: Subject to any disclaimer, the term of this patent is extended or adjusted under 35 U.S.C. 154(b) by 0 days.

(21) Appl. No.: 09/762,124

(22) PCT Filed: Jan. 31, 2000

(86) PCT No.: PCT/EP00/00748

§ 371 (c)(1), (2), (4) Date: Feb. 2, 2001

(87) PCT Pub. No.: WO00/75147

PCT Pub. Date: Dec. 14, 2000

(30) Foreign Application Priority Data

Jun. 7, 1999 (EP) ............................................. 99201802

(51) Int. Cl.$^7$ .............................. C07F 7/00; C07F 5/00; C07F 11/00; B01J 31/00

(52) U.S. Cl. ................................. 556/51; 556/1; 556/9; 556/10; 556/20; 556/28; 556/42; 556/57; 534/11; 534/15; 502/103; 502/117; 526/126; 526/160

(58) Field of Search ............................... 556/9, 10, 20, 556/28, 42, 51, 57, 1; 534/11, 15; 502/103, 117; 526/126, 160

(56) References Cited

U.S. PATENT DOCUMENTS

| | | | | |
|---|---|---|---|---|
| 5,908,947 | A | * 6/1999 | Vaartstra | 534/15 |
| 6,255,419 | B1 | * 7/2001 | Imuta et al. | 502/104 |
| 6,333,292 | B1 | * 12/2001 | Gibson et al. | 502/102 |

FOREIGN PATENT DOCUMENTS

| | | |
|---|---|---|
| EP | 0241560 | 10/1987 |
| EP | 0575875 | 12/1993 |
| WO | 9602580 | 2/1996 |
| WO | 9627439 | 9/1996 |
| WO | 9921899 | 5/1999 |
| WO | 0121674 | 3/2001 |

OTHER PUBLICATIONS

R. Baumann et al., J. Am. Chem. Soc., 121: 7822–7836 (1999).

R. R. Shrock, et al., Organometallics, 17(26): 5591–5593 (1998).

J. Okuda, et al., Chem. Ber., 128: 221–227 (1995).

R. R. Shrock et al., Organometallics, 17: 4795–4812 (1998).

D. McConville et al., Journal of Molecular Catalysis, A: Chemical 128: 201–214 (1998).

* cited by examiner

*Primary Examiner*—Porfirio Nazario-Gonzalez

(57) ABSTRACT

A new process, particularly simple, convenient and practical, for the direct synthesis of organometallic compounds of formula(I):

$$(A)(ZR^1{}_m)_n(A')ML_pL'_q \qquad (I)$$

wherein $(ZR^1{}_m)_n$ is a divalent group bridging A and A'; A and A' re independently —O—, —S—, or —N(R$^2$)—, wherein R$^2$ is hydrogen, alkyl, cycloalkyl, aryl, alkylaryl or arylalkyl; M is a transition metal belonging to group 3, 4, 5, 6 or to the lanthanide or actinide groups; L is a monoanionic sigma ligand, such as alkyl, cycloalkyl, aryl, alkylaryl or arylalkyl, optionally containing Si or Ge; L' is halogen or —OR$^3$, R$^3$ being an hydrocarbon radical; m is 0, 1 or 2; n is 1–8; p is 1–3; q is 0–2. Said process comprises reacting the ligand (H—A)(ZR$^1{}_m)_n$(A'—H) with about 1 molar equivalent of ML'$_s$ in the presence of about (2+p) molar equivalents of L$_j$B or LMgL', wherein B is an alkaline or alkaline-earth metal, s ranges from 3 to 6, and j is 1 or 2.

11 Claims, No Drawings

PREPARATION OF TRANSITION-METAL-ALKYL-COMPLEXES CARRYING A BIDENTATE, DIANIONIC LIGAND

The present invention relates to a new process, particularly simple, convenient and practical, for the preparation of organometallic complexes; more specifically, it relates to a process for the direct synthesis of non-cyclopentadienyl Group IV metal complexes, wherein the metal atom is linked to two sigma ligands selected from the group consisting of linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing Si or Ge atoms.

These complexes are useful as catalyst components, e.g. in the polymerization, oligomerization and hydrogenation of olefins, in association with alumoxanes and/or compounds able to form alkylmetal cations.

PRIOR ART DISCLOSURE

Homogeneous catalytic systems based on Group IV metal complexes containing chelating diamido or dialkoxide ligand systems are well known in the state of the art and their use in olefin polymerization reactions has recently received increasing attention. These complexes are usually employed as dihalide or dialkyl derivatives, in association with suitable cocatalysts, such as alumoxanes and borate salts; dichloride metal complexes are the most commonly used derivatives.

Dialkyl metal complexes are synthesized by passing through the corresponding dihalide derivatives, which are hydrocarbylated by ligand exchange with an appropriate hydrocarbylating agent to the target products; total yields are generally unsatisfactory and the following process steps are required:

(1) preparing the dihalide metal coordination complex by reacting a suitable ligand, usually silylated or derivatized with suitable leaving groups, with $MX_4$ (usually $TiCl_4$ or $ZrCl_4$);

(2) converting the dihalide complex obtained in step (1) into the corresponding dialkyl complex, by substitution of the halogens linked to the metal atom with the desired alkyl or aryl groups, by means of an alkylating agent such as alkyllithium, dialkylmagnesium or the corresponding Grignard reagent.

Therefore, dialkyl complexes can not be expediently synthesized by the existing methodology. For instance, J. Okuda et al. (*Chem. Ber.* 128: 221–227, 1995) described the preparation of a class of titanium complexes containing bidentate bis(phenoxy) ligands; dimethyl complexes were synthesized by the reaction of the corresponding dichloride derivatives with Grignard reagents, such as methylmagnesium bromide, at –78° C.

D. McConville and coworkers (*Journal of Molecular Catalysis A: Chemical* 128:201–214, 1998) described the reaction of $RHN(CH_2)_3NHR$ (wherein R is aryl) with 2 equivalents of BuLi, at –78° C., followed by 2 equivalents of $ClSiMe_3$, at 0° C., to produce the silylated diamine ligand $R(Me_3Si)N(CH_2)_3N(SiMe_3)R$; this diamine ligand was then treated with $TiCl_4$ to yield the dichloride complex $[RN(CH_2)_3NR]TiCl_2$ in unsatisfactory yields. Without the previous silylation of said diamine ligand, the reaction of the ligand dilithium derivative with $TiCl_4(THF)_2$ gave very low yields (<10%). The dichloride complex $[RN(CH_2)_3NR]TiCl_2$ was then reacted with 2 equivalents of MeMgBr, to give the dimethyl derivative $[RN(CH_2)_3NR]TiMe_2$. These complexes are active catalysts for the polymerization of α-olefins, and in particular 1-hexene.

With regard to alternative synthetic strategies for the production of metal diarnido complexes, the $M(NR_2)_4$ precursor amine elimination approach has provided in general a more efficient preparation than conventional salt elimination synthetic routes (see R. Schrock et al., *Organometallics*, 17:4795–4812, 1998).

However, this route usually leads to a myriad of undesired products and, for subsequent catalysis, it is critical that the amido complexes be converted to dichloride or dialkyl polymerization catalyst precursors, because amido-derived catalysts are significantly less active than chloride or alkyl-derived catalysts.

More specifically, as reported by R. Schrock in the cited reference, the reaction between $M(NMe_2)_4$ and a diamine ligand produced the corresponding $M(NMe_2)_2$ complex, which was then reacted with an excess of $Me_3SiCl$ in ether to form the $MCl_2$ complex; finally, the dichloride species was alkylated by using a Grignard reagent to afford the corresponding dialkyl complex, in unsatisfactory final total yields.

Also in this case, in order to achieve the desired dialkyl metal complex, it is necessary to pass through the metal dihalide derivative, thus requiring numerous reaction steps and lowering total reaction yields. Therefore, the prior art processes for producing metal complexes having hydrocarbon sigma ligands bonded to the central metal atom are inadequate for a commercially viable and practical production of said complexes, for use as catalyst components in olefin polymerization; it is felt the need for a simpler and more convenient and practical method to produce these complexes in satisfactory yields.

SUMMARY OF THE INVENTION

The Applicant has now unexpectedly found a new process for the preparation of organometallic complexes of formula (I):

$$(A)(ZR^1_m)_n(A')ML_pL'_q \qquad (I)$$

wherein:

$(ZR^1_m)_n$ is a $C_1$–$C_{50}$ divalent group bridging A and A', Z being C, Si, Ge, N, P, O or S; the $R^1$ groups, equal or different from each other, are hydrogen or linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups; two or more $R^1$ may form together one or more saturated, unsaturated or aromatic rings;

m is 0, 1 or 2, and more specifically it is 0 when Z is O or S, it is 1 when Z is N or P, and it is 2 when Z is C, Si or Ge;

n is an integer ranging from 1 to 8;

A and A', the same or different from each other, are divalent anionic groups selected from —O—, —S— and —N($R^2$)—, wherein $R^2$ is hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, optionally containing one or more atoms belonging to Groups 13–17 of the Periodic Table;

M is a transition metal belonging to group 3, 4, 5, 6 or to the lanthanide or actinide groups of the Periodic Table of the Elements (IUPAC version);

the substituents L, the same or different from each other, are monoanionic sigma ligands selected from the group consisting of linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl groups, optionally containing one or more Si or Ge atoms; preferably, the substituents L are the same;

the substituents L', the same or different from each other, are halogens or —OR$^3$, wherein R$^3$ is hydrogen or a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl group;

p is an integer ranging from 1 to 3; q is an integer ranging from 0 to 2, p+q being equal to the oxidation state of the metal M minus 2, and p+q being $\leq 3$;

said process comprising the following steps:

(1) reacting a ligand of formula (H—A)(ZR$^1_m$)$_n$(A'—H) with about (2+p) molar equivalents of a compound of formula L$_j$B or LMgL', wherein A, A', Z, R$^1$, m, n, p, L and L' have the meaning reported above; B is an alkaline or alkaline-earth metal; and j is 1 or 2, j being equal to 1 when B is an alkaline metal, and j being equal to 2 when B is an alkaline-earth metal; and (2) reacting the product obtained from step (1) with about 1 molar equivalent of a compound of formula ML'$_s$, wherein M and L' have the meaning reported above; s is an integer corresponding to the oxidation state of the metal and ranges from 3 to 6.

DETAILED DESCRIPTION OF THE INVENTION

The process of the invention allows organometallic complexes to be obtained, wherein the metal bears one or more sigma-bonded hydrocarbon substituents, in a simple, rapid and economic way, leading to the desired products in one reactor, starting from the suitable ligands. Moreover, said process leads to final yields much higher than the ones obtainable with the procedures known in the state of the art, therefore allowing a convenient industrial exploitation of the above organometallic complexes as catalyst components in the polymerization of olefins. In the complexes of formula (I), the divalent bridge (ZR$^1_m$)$_n$ is preferably selected from the group consisting of —CR$^1_2$—, —CR$^1_2$—SiR$^1_2$—,

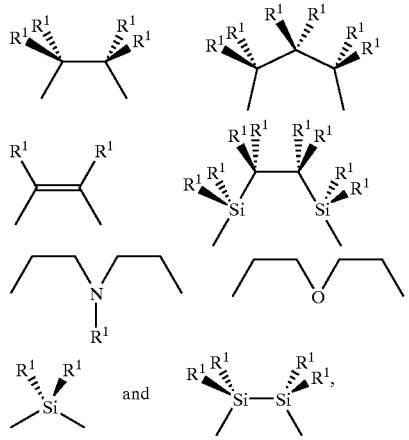

R$^1$ having the meaning reported above; more preferably, said divalent bridge is —Si(CH$_3$)$_2$—, —SiPh$_2$—, —Si(CH$_3$)$_2$—Si(CH$_3$)$_2$—, —CH$_2$—, —(CH$_2$)$_2$—, —(CH$_2$)$_3$— or —C(CH$_3$)$_2$—.

The variable m is 0, 1 or 2; the variable n ranges from 1 to 8 and, when n>1, the atoms Z can be different from each other, such as for instance in divalent bridges —CH$_2$—O—, —CH$_2$—S— and —CH$_2$—Si(CH$_3$)$_2$— (when n=2).

According to preferred embodiments of the process of the invention, in said divalent bridge (ZR$^1_m$)$_n$, two or more R$^1$ groups form together one or more saturated, unsaturated or aromatic rings, optionally condensed.

Examples of preferred divalent bridges are the following:

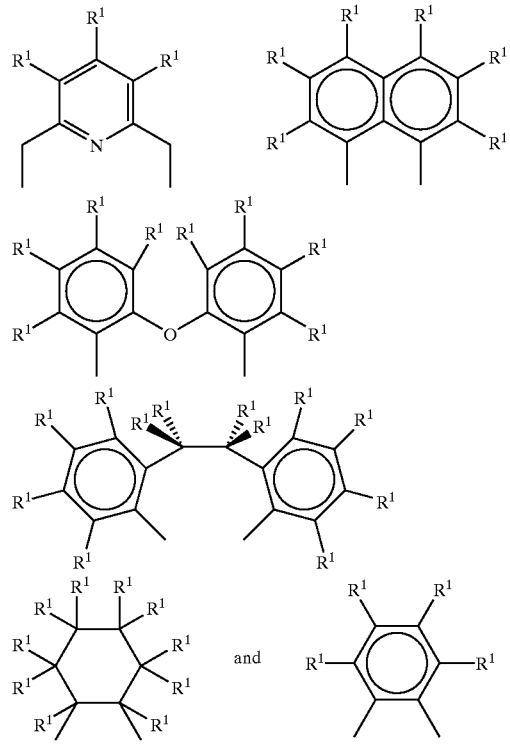

wherein the R$^1$ groups have the meaning reported above.

The groups A and A', the same or different from each other, are selected from —O—, —S— and —N(R$^2$)—, wherein R$^2$ is defined as above; said groups A and A' are preferably the same and are preferably —N(R$^2$)— or —O—, i.e. an amido or an alkoxy group, wherein R$^2$ is a linear or branched $C_1$–$C_{10}$ alkyl, a $C_7$–$C_{15}$ alkylaryl or a $C_7$–$C_{15}$ arylalkyl, optionally containing one or more heteroatoms belonging to Groups 13–17 of the Periodic Table, such as B, Si, GE, O, S, N, P, Cl and Br; even more preferably, R$^2$ is selected from the group consisting of methyl, ethyl, propyl, butyl, pentyl, hexyl and isomers of these alkyl radicals, norbornyl, benzyl, phenyl, 2,6-dialkyl-phenyl (such as 2,6-dimethyl-phenyl and 2,6,-diisopropyl-phenyl), 2,4,6-trialkyl-phenyl (such as 2,4,6-trimethyl-phenyl), trialkyl-silyl (such as trimethyl-silyl and triisopropyl-silyl) and diaryl-boryl (such as dimesityl-boryl).

The group R$^2$ may optionally contain —OR', SR', —NR'$_2$ or —PR'$_2$ groups, wherein R' is a $C_1$–$C_{10}$ alkyl group; the presence of this addition weak neutral donor site within the chelating cyclopentadienyl ligand framework may give rise to a tridentate ligand complex; more preferably, the donor group is —OMe, —OEt or —NMe$_2$.

The metal M is preferably Ti, Zr or Hf, and more preferably Ti.

The substituents L are preferably the same and are preferably selected from the group consisting of $C_1$–$C_7$ alkyl, $C_6$–$C_{14}$ aryl and $C_7$–$C_{14}$ arylalkyl groups, optionally containing one or more Si or Ge atoms; even more preferably, the substituents L are selected from the group consisting of methyl, ethyl, n-butyl, sec-butyl, phenyl, benzyl and —CH$_2$Si(CH$_3$)$_3$. According to a favorite embodiment of the invention, L is methyl.

The substituents L' are preferably Cl, Br or OR$^3$, wherein R$^3$ has the meaning reported above, and more preferably it is a C$_1$–C$_6$ alkyl or a C$_6$–C$_{10}$ aryl; even more preferably, L' is selected from the group consisting of Cl, Br, —OMe, —OEt, —OPr, —OBu and —OBz.

The process according to the present invention comprises the following steps:

(1) reacting a ligand of formula (H—A)(ZR$^1_m$)$_n$(A'—H) with about (2+p) molar equivalents of a compound of formula L$_j$B or LMgL', wherein A, A', Z, R$^1$, m, n, p, L and L' have the meaning reported above; B is an alkaline or alkaline-earth metal; and j is 1 or 2, j being equal to 1 when B is an alkaline metal, and j being equal to 2 when B is an alkaline-earth metal; and (2) reacting the product obtained from step (1) with about 1 molar equivalent of a compound of formula ML'$_s$, wherein M and L' have the meaning reported above, and s is an integer corresponding to the oxidation state of the metal and ranges from 3 to 6.

The organometallic complexes of formula (I) can be finally isolated from the reaction mixture obtained in step (2) and optionally purified according to standard procedures. Said process allows to obtain the complexes of formula (I) in very high yields, by means of a very practical and convenient one-pot reaction.

The ligand of formula (H—A)(ZR$^1_m$)$_n$(A'—H), wherein A, A', Z, R$^1$, m and n have the meaning reported above, may be synthesized according to procedures known in the state of the art. For instance, suitable bridged bis-amine ligands may be prepared as described in WO 96/27439. Moreover, suitable bridged bis-hydroxy ligands may be prepared as described in EP-A-241,560 (see ligands corresponding to formulae (I), (II), (III), (IV), (V) and (VI)). In the reactant ML'$_s$, the metal M is preferably Ti, Zr or Hf, and the substituents L' are preferably the same and are selected from the group consisting of —Cl, —Br, —OMe, —OEt, —OPr, —OBu and —OBz; the variable s ranges from 3 to 6 and corresponds to the oxidation state of the metal M. Said reactant is preferably selected from the group consisting of TiCl$_4$, ZrCl$_4$, HfCl$_4$, ScCl$_3$, YCl$_3$, NbCl$_5$, Ti(OEt)$_4$, Ti(OPr)$_4$, Ti(OBz)$_4$, Zr(OEt)$_4$, Zr(OPr)$_4$, Zr(OBz)$_4$, Zr(OEt)$_3$Cl, Hf(OEt)$_4$, Hf(OPr)$_4$ and Hf(OBz)$_4$; this reactant can be used even in the form of a stabilized derivative, such as an etherate complex of ML'$_s$, easily available on the market. L$_j$B and LMgL' are alkylating agents, wherein L is preferably a C$_1$–C$_7$ alkyl group, a C$_6$–C$_{14}$ aryl group or a C$_7$–C$_{14}$ arylalkyl group, optionally substituted with Si or Ge, and more preferably L is selected from the group consisting of methyl, ethyl, n-butyl, sec-butyl, phenyl, benzyl and —CH$_2$Si(CH$_3$)$_3$; even more preferably, L is methyl.

In the compound L$_j$B, B is an alkaline or alkaline-earth metal, and preferably Li or Mg; j can be 1 or 2, as already reported.

The compound LMgL' is a Grignard reagent, wherein Mg is magnesium and L and L' have the meanings reported above; L' is preferably Cl or Br.

According to a preferred embodiment of the process of the invention, said alkylating agent is methyllithium.

The molar ratio of the compound of formula L$_j$B or LMgL' to the ligand of formula (H—A)(ZR$^1_m$)$_n$(A'—H) can vary within wide limits; an improved process for obtaining dihydrocarbyl organometallic complexes of formula (I), wherein p=2 and q=0, is obtained at a ratio of about 4:1 and higher; an improved process for obtaining monohydrocarbyl complexes of formula (I), wherein p=1 and q=1, is obtained at a ratio of about 3:1.

The molar ratio of the compound of formula ML'$_s$ to the ligand of formula (H—A)(ZR$^1_m$)$_n$(A'—H) is preferably about 1:1.

According to a preferred embodiment, the process of the invention is carried out in an aprotic solvent, either polar or a polar; said aprotic solvent is preferably an aromatic or aliphatic hydrocarbon or an ether, and more preferably it is selected from the group consisting of benzene, toluene, pentane, hexane, heptane, cyclohexane, diethylether, tetrahydrofuran and mixtures thereof.

According to a preferred embodiment of the process of the invention, in step (1), said ligand (H—A)(ZR$^1_m$)$_n$(A'—H) is previously dissolved in an aprotic solvent and to the resulting solution is added the alkylating agent L$_j$B or LMgL'; this addition is preferably carried out at a temperature ranging from −80° C. to +50° C., and more preferably from −50° C. to +30° C. The alkylating agent is preferably added in the form of a solution in one of the above mentioned aprotic solvents.

The thus obtained reaction mixture is then allowed to react, under stirring, at a temperature preferably comprised between −80° C. and +50° C., more preferably between −50° C. and +30° C., and even more preferably at room temperature.

Before the reaction with ML'$_s$ in step (2), the mixture obtained from step (1) has preferably a temperature ranging from −80° C. to +50° C., and more preferably it is cooled to a temperature ranging from −50° C. to room temperature; then, ML'$_s$ is quickly added to the cooled mixture, in the form of a solution in one of the above mentioned aprotic solvents, preferably pentane.

The reaction mixture is then allowed to react at a temperature comprised between −80° C. and +50° C., more preferably between −50° C. and +30° C., and even more preferably at room temperature. The thus obtained organometallic complexes of formula (I) can be isolated according to procedures known in the state of the art.

These organometallic complexes are useful in addition oligomerization and polymerization processes wherein, in association with an activating cocatalyst, they are contacted with one or more addition polymerizable monomers.

Addition polymerizable monomers include ethylenically unsaturated monomers, conjugated or non-conjugated dienes and polyenes. The above organometallic complexes are particularly useful in homo and co-polymerization of α-olefins of formula CH$_2$=CHR, wherein R is hydrogen or a C$_1$–C$_{20}$ alkyl, such as propylene, 1-butene, 1-pentene, 4-methyl-1-pentene, 1-hexene and 1-octene; preferably said α-olefin is 1-hexene.

As reported above, the organometallic complexes obtained with the process of the invention form suitable polymerization catalytic systems in association with activating cocatalysts, such as alumoxanes, aluminium alkyls, aluminium halides, aluminium alkylhalides, Lewis acids, ammonium salts, non-interfering oxidizing agents and mixtures thereof.

Preferably the ratio of the organometallic complex and the cocatalyst on a molar basis is from about 1:0.1 to about 1:10,000, and more preferably from 1:1 to 1:1,000.

Suitable activating cocatalysts are linear alumoxanes having the following formula:

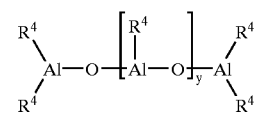

wherein the substituents R$^4$, the same or different from each other, are selected from the group consisting of halogen, linear or branched, saturated or unsaturated C$_1$–C$_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing Si and Ge atoms, and y ranges from 0 to 40; $R^4$ is preferably methyl, ethyl, isobutyl or 2,4,4-trimethyl-pentyl; or cyclic alumoxanes having the following formula:

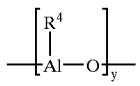

wherein $R^4$ has the meaning herein described and y is an integer ranging from 2 to 40. Examples of alumoxanes suitable as activating cocatalysts in the catalysts according to the present invention are methylalumoxane (MAO), tetra-isobutyl-alumoxane (TIBAO), tetra-2,4,4-trimethylpentylalumoxane (TIOAO) and tetra-2-methyl-pentylalumoxane. Mixtures of different alumoxanes can also be used.

Suitable activating cocatalysts are also the products of the reaction between water and an organometallic aluminum compound, preferably of formula $AlR^4_3$ or $Al_2R^4_6$, wherein $R^4$ has the meaning reported above. Particularly suitable are the organometallic aluminum compounds of formula (II) described in EP-A-575,875, those of formula (II) described in WO 96/02580, those described in WO 99/21899 and in the European app. no. 99203110.4. Mixtures of different organometallic aluminum compounds can also be used.

Further suitable activating cocatalysts are those compounds capable of forming an alkylmetal cation; preferably, said compounds have formula $Y^+Z^-$, wherein $Y^+$ is a Bronsted acid capable of donating a proton and of reacting irreversibly with a substituent X of the compound of formula (I), and $Z^-$ is a compatible non-coordinating anion, capable of stabilizing the active catalytic species which result from the reaction of the two compounds, and which is sufficiently labile to be displaceable by an olefinic substrate. Preferably, the $Z^-$ anion comprises one or more boron atoms. More preferably, the anion $Z^-$ is an anion of formula $BAr_4^{(-)}$, wherein the Ar substituents, the same or different from each other, are aryl radicals such as phenyl, pentafluorophenyl, bis(trifluoromethyl)phenyl. Tetrakis-pentafluorophenylborate is particularly preferred. Moreover, compounds of formula $BAr_3$ can be conveniently used.

The polymerization process may be carried out in liquid phase, optionally in the presence of an inert hydrocarbon solvent either aromatic (e.g. toluene) or aliphatic (e.g. propane, hexane, heptane, isobutane, cyclohexane or 2,2,4-trimethylpentane), or in the gas phase.

The polymerization is conducted according to known techniques for Ziegler-Natta or Kaminsky-Sinn type polymerization, at a temperature generally ranging from about –30° C. to about 250° C., and preferably from 20 to 150° C., at reduced, elevated or atmospheric pressures. The molecular weight of the polymers can be varied by changing the type or the concentration of the catalytic components or by using molecular weight regulators, for example hydrogen. The catalyst may be used as it is, or supported on a suitable organic or inorganic support, to provide a heterogeneous supported catalyst.

The following examples are given for illustrative and not limiting purposes.

General Procedures and Characterizations

All operations were performed under nitrogen by using conventional Schlenk-line techniques. Solvents were purified by degassing with nitrogen and passing over activated alumina and subsequently stored under nitrogen. MeLi (Acros) and $TiCl_4$ were used as received.

The compounds were analyzed by $^1$H-NMR by using a AC200 Bruker spectrometer, operating at 200.13 MHz. All NMR solvents were dried over $P_4O_{10}$ and distilled before use. Preparation of the samples was carried out under nitrogen, using standard inert atmosphere techniques.

EXAMPLE 1

Synthesis of $CH_2$(6-t-Bu-4-Me-phenoxy)$_2$TiMe$_2$ 2.0 g of 2,2'-methylenebis(4-Me-6-t-Bu-phenol) (5.9 mmol) were dissolved in 50 mL Et$_2$O in a 100 mL Schlenk tube, and the solution cooled to –80° C. 14.7 mL of 1.6 M MeLi in Et$_2$O (23.5 mmol) were added dropwise, over 15 minutes, with stirring. The solution was allowed to warm to room temperature and then stirred for 2 hours. A light yellow solution was obtained. 0.65 mL of TiCl$_4$ (Aldrich 99%, 5.9 mmol) were dissolved in 50 mL of pentane. The two solutions were both cooled to –80° C. and the TiCl$_4$ solution in pentane was quickly added to the Li salt in Et$_2$O. The reaction mixture was allowed to warm slowly to room temperature overnight (about 16 hours) and a dark green suspension was finally obtained. The reaction mixture was then brought to dryness under reduce pressure. The thus obtained dark green solid was extracted with 100 mL of pentane in a Soxhlet apparatus and then the filtrate was evaporated to dryness under reduced pressure to leave 1.7 g of light-yellow target product $CH_2$(6-t-Bu-4-Me-phenoxy)$_2$TiMe$_2$.

Isolated yield 70%.

$^1$H NMR ($C_6D_6$, δ, ppm): 1.358 (s, 3H, Ti—CH$_3$), 1.374 (s, 3H, Ti—CH$_3$), 1.604 (s, 18H, t-Bu), 2.108 (s, 6H, Ar—CH$_3$), 3.21 (AB system, J=14.20 Hz, 1H, CH$_2$), 3.38 (AB system, J=14.20 Hz, 1H, CH$_2$), 6.98–7.02 (m, 4 H, Ar—H).

EXAMPLE 2

Synthesis of N,N'-di-t-butyl-ethylendiamido titanium monochloro monomethyl 3 g of N,N'-di-t-butyl-ethylendiamine (Aldrich 98%, 17.06 mmol) were dissolved in 40 mL Et$_2$O, in a 100 mL Schlenk tube, and the solution was cooled to –80° C. 42.7 mL of 1.6 M MeLi in Et$_2$O (68.3 mmol) were added dropwise, over 15 minutes, with stirring. The solution was allowed to warm to room temperature and then stirred for 2 hours. A light yellow solution was obtained. 1.91 mL of TiCl$_4$ (Aldrich 99%, 17.42 mmol) were dissolved in 40 mL of pentane. The two solutions were both cooled to –80° C. and the TiCl$_4$ solution in pentane was quickly added to the Li salt in Et$_2$O. The reaction mixture was allowed to warm slowly to room temperature overnight (about 16 hours) and a brown suspension was finally obtained. The reaction mixture was then brought to dryness under reduce pressure. The thus obtained brown solid was extracted with 100 mL of pentane in a Soxhlet apparatus and then the filtrate was evaporated to dryness under reduced pressure, thus giving 3 g of dark-brown oil, which at the $^1$H-NMR analysis resulted to be a mixture of chloromethyl and dimethyl N,N' di-t-butylethylendiamido titanium. Crystallization from pentane yielded 0.2 g of orange N,N' di-t-butyl-ethylendiamido titanium monochloro monomethyl.

What is claimed is:

1. A process for the preparation of organometallic complexes of formula (I):

wherein $(ZR^1_m)_n$ is a $C_1$–$C_{50}$ divalent group bridging A and A', Z being C, Si, Ge, N, P, O or S; the $R^1$ groups, the same or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl groups, two or more $R^1$ groups optionally forming together one or more saturated, unsaturated or aromatic rings;

m is 0, 1 or 2; n is an integer ranging from 1 to 8;

A and A', the same or different from each other, are divalent anionic groups selected from —O—, —S— and —N($R^2$)—, wherein $R^2$ is hydrogen, a linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl or $C_7$-$C_{20}$ arylalkyl, optionally containing one or more atoms belonging to Groups 13–17 of the Periodic Table;

M is a transition metal belonging to group 3, 4, 5, 6 or to the lanthanide or actinide groups of the Periodic Table of the Elements;

the substituents L, the same or different from each other, are monoanionic sigma ligands selected from the group consisting of linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl and $C_7$-$C_{20}$ arylalkyl groups, optionally containing one or more Si or Ge atoms;

the substituents L', the same or different from each other, are halogens or —O$R^3$, wherein $R^3$ is selected from the group consisting of hydrogen, linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl and $C_7$-$C_{20}$ arylalkyl groups;

p is an integer ranging from 1 to 3; q is an integer ranging from 0 to 2, p+q being equal to the oxidation state of the metal M minus 2, and p+q being $\leq 3$;

said process comprising the following steps:

(1) reacting a ligand of formula (H—A)(Z$R^1_m$)(A'—H) with about (2+p) molar equivalents of a compound of formula $L_jB$ or LMgL', wherein A, A', Z, $R^1$, m, n, p, L and L' have the meaning reported above; B is an alkaline or alkaline-earth metal; and j is 1 or 2, j being equal to 1 when B is an alkaline metal, and j being equal to 2 when B is an alkaline-earth metal; and (2) reacting the product obtained from step (1) with about 1 molar equivalent of a compound of formula ML'$_s$, wherein M and L' have the meaning reported above; s is an integer corresponding to the oxidation state of the metal and ranges from 3 to 6.

2. The process according to claim 1, wherein said divalent group (Z$R^1_m$)$_n$ is selected from the group consisting of —C$R^1_2$—, —C$R^1_2$—Si$R^1_2$—,

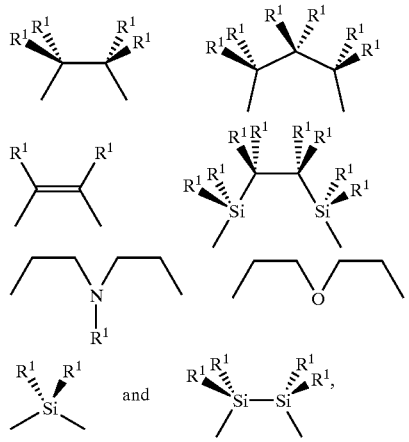

wherein $R^1$ has the meaning reported in claim 1.

3. The process according to claim 1, wherein said divalent group (Z$R^1_m$)$_n$ is selected from the group consisting of:

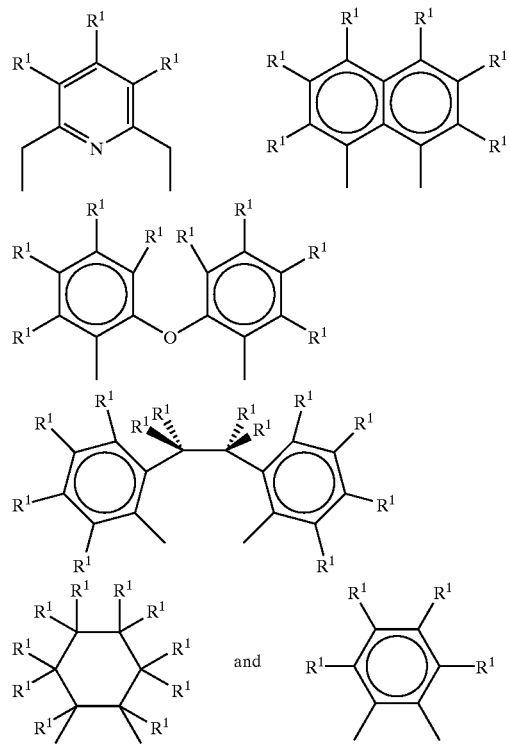

wherein the $R^1$ groups have the meaning reported in claim 1.

4. The process according to claim 1, wherein the divalent anionic groups A and A' are the same and are —N($R^2$)— or —O—, and —$R^2$ is selected from the group consisting of methyl, ethyl, propyl, butyl, pentyl, hexyl and isomers of these alkyl radicals, norbornyl, benzyl, phenyl, 2,6-dialkyl-phenyl, 2,4,6-trialkyl-phenyl, trialkyl-silyl and diaryl-boryl.

5. The process according to claim 1, wherein the substituents L are the same and are selected from the group consisting of methyl, ethyl, n-butyl, sec-butyl, phenyl, benzyl and —CH$_2$Si(CH$_3$)$_3$.

6. The process according to claim 1, wherein L' is selected from the group consisting of Cl, Br, —OMe, —OEt, —OPr, —OBu and —OBz.

7. The process according to claim 1, wherein said compound of formula ML'$_s$ is selected from the group consisting of TiCl$_4$, ZrCl$_4$, HfCl$_4$, SeCl$_3$, YCl$_3$, NbCl$_5$, Ti(OEt)$_4$, Ti(OPr)$_4$, Ti(OBz)$_4$, Zr(OEt)$_4$, Zr(OPr)$_4$, Zr(OBz)$_4$, Zr(OEt)$_3$Cl, Hf(OEt)$_4$, Hf(OPr)$_4$, Hf(OBz)$_4$ and etherate complexes thereof.

8. The process according to claim 1 wherein, in the compound $L_jB$ or LMgL', L is selected from the group consisting of methyl, ethyl, n-butyl, sec-butyl, phenyl, benzyl and —CH$_2$Si(CH$_3$)$_3$; B is Li or Mg; and L' is Cl or Br.

9. The process according to claim 8, wherein L is methyl.

10. The process according to claim 1, characterized by being carried out in an aprotic solvent.

11. The process according to claim 10, wherein said aprotic solvent is selected from the group consisting of benzene, toluene, pentane, hexane, heptane, cyclohexane, diethylether, tetrahydrofuran and mixtures thereof.

* * * * *

UNITED STATES PATENT AND TRADEMARK OFFICE
CERTIFICATE OF CORRECTION

PATENT NO.   : 6,441,211 B1
DATED        : August 27, 2002
INVENTOR(S)  : Luigi Resconi It is certified that error appears in the above-identified patent and that said Letters Patent is hereby corrected as shown below:

Column 10,
Line 49, change "$SeCl_3$" to -- $ScCl_3$ --

Signed and Sealed this

Eleventh Day of January, 2005

JON W. DUDAS
*Director of the United States Patent and Trademark Office*